(12) United States Patent
Node et al.

(10) Patent No.: US 6,384,228 B2
(45) Date of Patent: *May 7, 2002

(54) METHOD FOR SYNTHESIS OF HALOPYRIDYL-AZACYCLOPENTANE DERIVATIVE AND INTERMEDIATE THEREOF

(75) Inventors: Manabu Node, Hirakata; Daisaku Nakamura, Ichihara; Toshio Fujiwara; Shogo Ichihashi, both of Kyoto, all of (JP)

(73) Assignee: Nihon Medi-Physics Co., Ltd., Hyogo-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/462,379

(22) PCT Filed: Sep. 3, 1998

(86) PCT No.: PCT/JP98/03954

§ 371 Date: Jan. 7, 2000

§ 102(e) Date: Jan. 7, 2000

(87) PCT Pub. No.: WO99/61443

PCT Pub. Date: Dec. 2, 1999

(30) Foreign Application Priority Data

May 26, 1998 (JP) .......................................... 10-143639

(51) Int. Cl.[7] ..................... C07D 211/70; C07D 209/52; C07C 67/00
(52) U.S. Cl. ....................... 546/329; 546/333; 548/452; 560/204
(58) Field of Search .............................. 546/329, 333; 548/452; 560/204

(56) References Cited

U.S. PATENT DOCUMENTS 5,461,127 A * 10/1995 Naganuma et al. ......... 526/127
6,143,845 A * 11/2000 Nakacho et al. ......... 524/124.7

OTHER PUBLICATIONS

Aso et al., "Preparation of Optically Active (R)– and (S)–Allene–1,3–dicarboxylates and their Asymmetric Cycladdtion Reaction eith Cyclopentadiene.", Tetrahedron Letters, vol. 33(39), pp. 5787–5790, 1992.*
Ikeda et al., "Structure and Asymmetric Diels–Alder Reactions of Optically Active Allene–1,3–dicarboxylates." J. Org. Chem., vol. 61, pp. 2031–2037, 1996.*
Pavri et al., "A new [4+2] Cycloaddition Strategy for the Synthesis of N–Acyl–7–Azabicyclo[2.2.1]Heptan–2–ones: A Formal Synthesis of epibatidine." Tetrahedron Letters, vol. 38(46), pp. 7993–7996, 1997.*
Pavri, Neville P. et al, A New [4+2]Cycloaddition Strategy for the Synthesis of N–Acyl–7–Azabicyclo[2.2.1] Heptan–2–Ones: A Formal Synthesis of (±)–Epibatidine, Tetrahedron Letters, 1997, vol. 38, No. 46, pp. 7993–7996.
Aso, Mariko et al, Preparation of Optically Active (R)– and (S)–Allene–1,3–dicarboxylates and Their Asymmetric Cycloaddition Reactions with Cyclopentadiene, Tetrahedron Letters, 1992, vol. 33, No. 39, pp. 5787–5790.
Ikeda, Izumi et al, Structure and Asymmetric Diels–Alder Reactions of Optically Active Allene–1,3–dicarboxylates, J. Org. Chem., 1996, vol. 61, No. 6, pp. 2031–2037.
Zhang, Chunming et al, A Short and Efficient Total Synthesis of (±)–Epibatidine, J. Org. Chem., 1996, vol. 61, No. 20, pp. 7189–7191.
Fletcher, Stephen R. et al, Total Synthesis and Determination of the Absolute Configuration of Epibatidine, J. Org. Chem., 1994, vol. 59, pp. 1771–1778.

* cited by examiner

Primary Examiner—Barbara P. Badio
(74) Attorney, Agent, or Firm—Sughrue Mion, PLLC

(57) ABSTRACT

The present invention relates to a method for synthesis of an optically active halopyridyl-azacyclo-pentane derivative and the intermediate thereof which comprises preparing an optically active allene-1,3-dicarboxylic acid ester derivative from an optically active acetonedicarboxylic acid ester derivative and then proceeding through a 7-azabicyclo [2.2.1]heptane derivative to obtain the objective product.

13 Claims, No Drawings

US 6,384,228 B2

METHOD FOR SYNTHESIS OF HALOPYRIDYL-AZACYCLOPENTANE DERIVATIVE AND INTERMEDIATE THEREOF

This application is a 371 of PCT/JP98/03954 filed Sep. 3, 1998.

TECHNICAL FIELD PERTINENT TO THE INVENTION

The present invention relates to a method for synthesis of halopyridyl-azacyclopentane derivative such as epibatidine, which is an alkaloid having a strong analgesic activity as its pharmacological effect, and the intermediate thereof. In more particular, the present invention relates to a novel method for synthesis of halopyridyl-azacyclopentane derivative and the intermediate thereof, which comprises preparing an optically active allene compound from an acetonedicarboxylic acid as a starting material, then preparing 7-azabicyclo[2.2.1]heptane derivative as an intermediate through Diels-Alder reaction of the optically active allene compound obtained above with pyrrole, so as to prepare halopyridyl-azacyclopentane derivative.

BACKGROUND ART (−)-Epibatidine, which is an alkaloid isolated from the skin of the Ecuadorian poison frog, is attracting attention as an analgesic agent of utterly new type because it has as its pharmacological effect a strong analgesic activity of about 200 times more potent than that of morphine and moreover it has been suggested that its analgesic action is exhibited without the intermediation of opioid receptor. On the other hand, though it has a strong toxicity, it possesses a very interesting physiological activity; for example, it has recently been revealed that it acts as an agonist for nicotinic acetylcholine receptors of the central nerve (Daly, J. W., et at., Mol. Pharm., 1994, 45, 563) and it has been disclosed that its radiolabelled form is useful as an imaging agent for nicotinic acetylcholine receptors (U.S. Pat. No. 5,726,189). In addition to the interesting physiological activities described above, (−)-epibatidine has a unique mother skeleton, 7-azabicyclo[2.2.1]heptane, so that a variety of methods for synthesizing the compound have been studied.

For example, attempts have been made to synthesize an intermediate having the 7-azabicyclo-[2.2.1]heptane core and obtain (+) and (−)-epibatidine therefrom through the alkylation of N-[(trifluoroacetyl)amino]cyclohex-3-ene (Fletcher, S. R. et al., J. Org. Chem., 1994, 59, 1771–1778), the Diels-Alder reaction of p-toluylsulfonyl-acetylene with N-(t-butoxycarbonyl)pyrrole (Carrol, F. I. et al., J. Med. Chem., 1997, 40, 2293–2295), the Diels-Alder reaction of methyl 3-bromopropiolate with N-(t-butoxycarbonyl)pyrrole (Zhang, C. et al., J. Org. Chem., 1996, 61, 7189–7179) and method of synthesis which uses levulinic acid as the starting material (Rapoport, H. et al., J. Org. Chem., 1995, 60, 2683–2691). These methods, however, have the disadvantage of very low yield because the racemate obtained must be subjected to optical resolution to obtain the intended optically active epibatidine. On the other hand, with regards to the asymmetric synthesis of epibatidine, there have been reported, for example, an asymmetric azidation which uses an asymmetric ligand and Pd (Trost, B. M. et al., Tetrahedron Lett., 1996, 37, 7485–7488), an asymmetric protonation which uses an asymmetric alcohol (Kosugi, H. F. et al., Chem. Commun., 1997, 1857–1858), an asymmetric desulfonation which uses an asymmetric amine (Simpkins, N. S. et al., Tetrahedron Lett., 1998, 39, 1023–1024) and an asymmetric oxidation which uses microbial oxidation (Olivo, H. F. et al., Tetrahedron Lett., 1998, 39, 1309–1312). However, these methods have disadvantages of requiring lengthy process steps or of a low optical purity of the product.

An allene compound is a useful substance which has the 1,2-diene structure and, by virtue of its unique reactivity, can be used for synthesis of various compounds in organic synthesis. A generally used method for synthesizing an allene compound is the substitution reaction starting from a propargyl compound which accompanies isomerization to an allene compound (Alexakis, A. et al., J. Am. Chem. Soc., 1990, 112, 8042–8047). Other known methods include a substitution reaction using a Grignard's reagent which starts from a dithioacetal derivative (Luh, T. Y. et al., J. Org. Chem., 1996, 61, 8685) and synthesis of an allene compound by Wittig reaction in which attention is directed to the species of ketene (Fuji, K. et al., Synlett, 1995,933), but these methods cannot be applied to the synthesis of allene-1,3-dicarboxylic acid derivatives. Further, a method has been reported (Bryson, T. A. et al., Org. Synth., 1988, coll. VI, 505) which comprises chlorinating diethyl 1,3-acetone dicarboxylate with phosphorus pentachloride and then treating the resulting product with triethylamine to obtain ethyl allene-1,3-dicarboxylate. This method, however, has the disadvantage of requiring lengthy process steps and of a low yield of the product.

With regard to the example of using an allene compound for synthesizing the bicyclo[2.2.1]heptane core, the synthesis of the bicyclo[2.2.1]heptane core through the Diels-Alder reaction of menthyl allenecarboxylate with cyclopentadiene has been reported (Kanematsu, K. et al., J. Org. Chem., 1996, 61, 2031). A method of synthesis has been recently reported that the 7-azabicyclo[2.2.1]heptane core is synthesized through the Diels-Alder reaction of methyl allenecarboxylate with a pyrrole derivative and the racemate of epibatidine is obtained therefrom (Trudell, M. L. et al., Tetrahedron Lett., 1997, 38, 7993–7996). This method also has the disadvantage of requiring an optical resolution step.

In view of the situations, the object of the present invention is to provide a method for synthesis of an optically active halopyridyl-azacyclopentane derivative wherein an optically active allene-1,3-dicarboxylic acid derivative and a 7-azabicyclo[2.2.1]-heptane core derivative are employed as the intermediates and wherein the synthesis routes are shortened, the operations are simple and a high optical yield can be obtained, and also a method for synthesis of the intermediates.

DISCLOSURE OF THE INVENTION

According to the present invention, there is provided a method for synthesis of a an optically active halopyridyl-azacyclopentane derivative which comprises the first step of allowing an optically active acetonedicarboxylic acid ester derivative to react in the presence of a basic substance and a dehydrating agent to obtain a diastereomer mixture of an allene-1,3-dicarboxylic acid ester derivative and then subjecting the diastereomer mixture to asymmetric transformation to obtain an optically active (R)- or (S)-allene-1,3-dicarboxylic acid ester derivative, the second step of subjecting the optically active allene-1,3-dicarboxylic acid ester derivative to an optically active Diels-Alder reaction with a dienophile to obtain a 7-azabicyclo[2.2.1]heptene derivative and then reducing the optically active 7-azabicyclo[2.2.1]heptene derivative to obtained an optically active 7-azabicyclo[2.2.1]heptane derivative, and the third step of preparing an optically active halopyridyl-azacyclopentane derivative from the optically active 7-azabicyclo[2.2.1]-heptane derivative.

More specifically, there is provided a method for synthesis of an optically active halopyridyl-azacyclopentane derivative, wherein the optically active acetone-dicarboxylic acid ester derivative is represented by the formula (1)

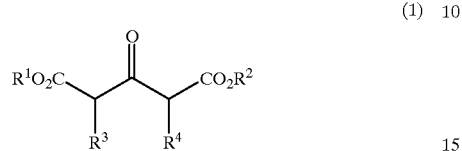

(1)

(wherein $R^1$ and $R^2$ are each a group derived from an optically active alcohol and $R^3$ and $R^4$ are each a member selected from the group consisting of a hydrogen atom, alkyl group and aryl group, which may be the same or different from each other), the optically active allene-1,3-dicarboxylic acid ester derivative is R- or S-enantiomer represented by the formula (2)

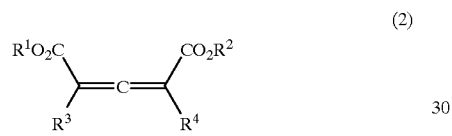

(2)

(wherein $R^1$ and $R^2$ are each a group derived from an optically active alcohol and $R^3$ and $R^4$ are each a member selected from the group consisting of a hydrogen atom, alkyl group and aryl group, which may be the same or different from each other), the optically active 7-azabicyclo[2.2.1]heptene derivative is represented by the formula (3), or its enantiomer represented by formula (4)

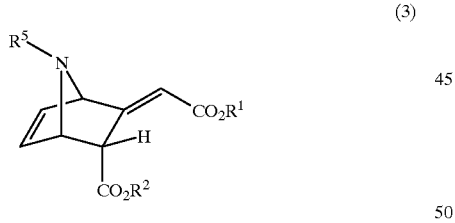

(3)

(wherein $R^1$ and $R^2$ are each a group derived from an optically active alcohol and $R^5$ is a protective group for an amino group),

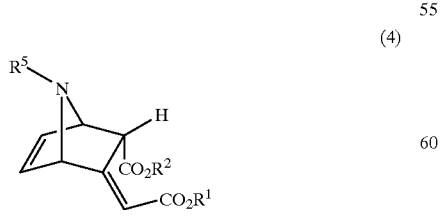

(4)

(wherein $R^1$ and $R^2$ are each a group derived from an optically active alcohol and $R^5$ is a protective group for an amino group), the optically active 7-azabicyclo[2.2.1]heptane derivative is a ketoester compound represented by the formula (5), or the its enantiomer represented by formula (6)

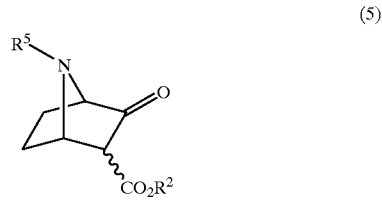

(5)

(wherein $R^2$ is a group derived from an optically active alcohol and $R^5$ is a protective group for an amino group),

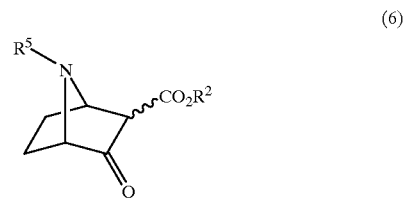

(6)

(wherein $R^2$ is a group derived from an optically active alcohol and $R^5$ is a protective group for an amino group), or is an optically active ketone compound represented by the formula (7) or its enantiomer represented by formula (7)';

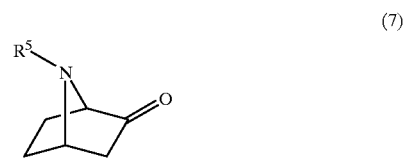

(7)

(wherein $R^5$ is a protective group for an amino group),

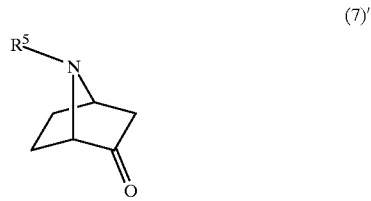

(7)'

(wherein $R^5$ is a protective group for an amino acid), and;

the optically active halopyridyl-azacyclopentane derivative is represented by the formula (8) or its enantiomer represented by formula (8)';

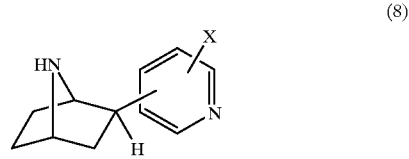

(8)

(wherein X is a halogen atom selected from Cl, F, Br and I or a radioactive isomer thereof),

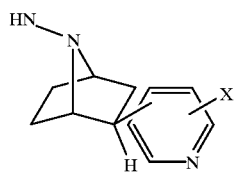

(8)'

(wherein X is a halogen atom selected from Cl, F, Br, and I or a radioactive isomer thereof).

The second aspect of the present invention relates to a method for synthesis of an optically active allene-1,3-dicarboxylic acid ester derivative, which is an intermediate for synthesis of the optically active halopyridyl-azabicyclo derivative. Thus, there is provided a method for synthesis of an optically active allene-1,3-dicarboxylic acid ester derivative which comprises subjecting an acetonedicarboxylic acid and an optically active alcohol to esterification in the presence of a basic substance and a dehydrating agent, or subjecting an acetonedicarboxylic acid ester (wherein the ester group is a lower alkyl or phenyl group) and an optically active alcohol to transesterification in the presence of a basic substance, to obtain an optically active acetone-dicarboxylic acid ester derivative, then subjecting the optically active acetonedicarboxylic acid ester derivative to alienation in the presence of a basic substance and a dehydrating agent to obtain a mixture of diastereomers of an allene-1,3-dicarboxylic acid ester derivative, and then subjecting the mixture of diasteromers to crystallization-induced asymmetric transformation with cooling and crystallization in the presence of a basic substance to obtain (R)-allene-1,3-dicarboxylic acid ester derivative or (S)-allene-1,3-dicarboxylic acid ester derivative.

Another aspect of the present invention relates to a method for synthesis of a ketoester compound or a ketone compound of an optically active 7-azabicyclo-[2.2.1]heptane derivative useful as a precursor of the halopyridyl-azacyclo derivative represented by the formula (8). Thus, a ketoester compound of the optically active 7-azabicyclo[2.2.1]heptane derivative represented by the formula (5) or its enantiomer of the formula (6) can be synthesized by subjecting the optically active allene-1,3-dicarboxylic acid ester derivative obtained by the above-mentioned method and a dienophile to Diels-Alder reaction to obtain the optically active 7-azabicyclo[2.2.1]heptene derivative represented by the formula (3) or its enantiomer of the formula (4), then selectively reducing the isolated olefin of the derivative, and subjecting the resulting product to ozone decomposition,

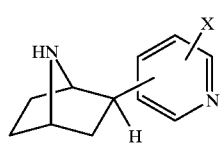

(8)

(wherein X is a halogen atom selected from Cl, F, Br and I or a radioactive isomer thereof),

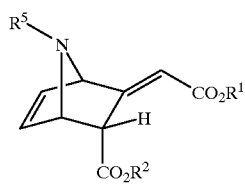

(3)

(wherein $R^1$ and $R^2$ are each a group derived from an optically active alcohol and $R^5$ is a protective group for an amino group),

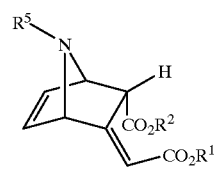

(4)

(wherein $R^1$ and $R^2$ are each a group derived from an optically active alcohol and $R^5$ is a protective group for an amino group),

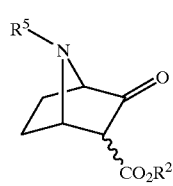

(5)

(wherein $R^2$ is a group derived from an optically active alcohol and $R^6$ is a protective group for an amino group),

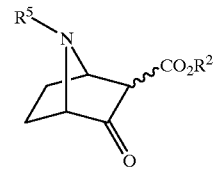

(6)

(wherein $R^2$ is a group derived from an optically active alcohol and $R^5$ is a protective group for an amino group).

Further, the optically active 7-azabicyclo-[2.2.1]heptan-2-one represented by the formula (7) can be obtained by further subjecting the ketoester compound of the optically active 7-azabicyclo[2.2.1]heptane-derivative represented by the formula (5) or the formula (6) to hydrolysis and decarbonation,

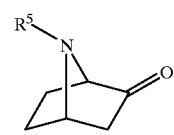

(7)

(wherein $R^5$ is a protective group for an amino group).

In the above-mentioned aspects, the optically active alcohol is preferably one selected from menthols, such as (−)-menthol, (+)-menthol and (+)-isomenthol, and binaphthol derivatives, such as (R)-(+)-1,1'-bi(2,2'-naphthol), (R)-(+)-1,1'-bi(2,2'-naphthol)monomethyl ester, (S)-(−)-1,1'-bi(2,2'-naphthol) and (S)-(−)-1,1'-bi(2,2'-naphthol) monomethyl ester; the dehydrating agent is preferably one selected from 2-chloro-1,3-dimethyl-imidazolium chloride, 2-chloro-1,3-dimethylimidazolinium hexafluorophosphate and the like, and the basic substance is preferably one selected from tertiary amines, such as triethylamine and dimethylaminopyridine.

According to the present invention, from an acetonedicarboxylic acid or its lower alkyl ester as the starting active alcohol or the transesterification of an acetonedicarboxylic acid alkyl ester or phenyl ester (I)-b with an optically active alcohol. When acetone-dicarboxylic acid (I)-a is used, for example (−)-menthol as the optically active alcohol and the carboxylic acid (I)-a are added to the methylene chloride solution of 2-chloro-1,3-dimethylimidazolinium chloride (hereinafter abbreviated as DMC), and pyridine is added dropwise thereto at room temperature to effect esterification, whereby optically active menthyl 1,3-acetonedicarboxylate (II) [R=(−)-menthyl group] is obtained.

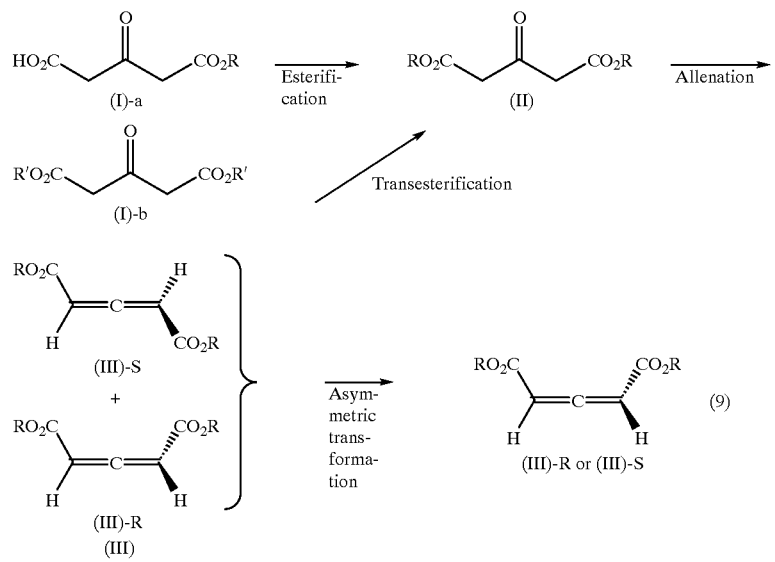

material, an optically active allene-1,3-dicarboxylic acid derivative having a high optical purity can be obtained, without conducting a complicated operation of optical resolution, through the synthesis of an optically active acetonedicarboxylic acid ester, effective synthesis of a mixture of diastereomers of optically active allene-1,3-dicarboxylic acid derivative by alienation reaction, and asymmetric crystallization of the mixture of diastereomers. By proceeding via the novel optically active allene-1,3-dicarboxylic acid derivative synthesis, the 7-azabicyclo[2.2.1]heptane derivative, which is the precursor of the halopyridyl-azacyclopentane derivative, can be synthesized with shortened synthesis steps and with a high yield, and thus a novel method for total synthesis of an optically active halopyridyl-azacyclopentane derivative which includes the above-mentioned synthesis steps can be provided.

BEST MODE FOR CARRYING OUT THE INVENTION

One mode of the synthesis route of the first step of the present invention is described below with reference to the formula (9), wherein R' is a lower alkyl group or phenyl group, and R is a group derived from an optically active alcohol.

In the formula (9), an optically active 1,3-acetonedicarboxylic acid ester (II) is obtained by the esterification of acetonedicarboxylic acid (I)-a with an optically At the stage of obtaining an optically active allene compound in the above-mentioned process step, the acetone dicarboxylic acid dialkyl ester (I)-b (e.g., R'=methyl or ethyl) is preferably refluxed together with a basic substance, such as dimethylaminopyridine in a solvent such as toluene, because thereby the transesterification proceeds easily and 1,3-acetone-dicarboxylic acid menthyl ester (II) is obtained in a quantitative yield. This is a preferable mode of reaction because an acetonedicarboxylic acid dialkyl ester is easily obtainable, the yield of transesterification is high and moreover the treatment after reaction can be easily conducted.

Then the optically active 1,3-acetone-dicarboxylic acid menthyl ester (II) is added dropwise under ice cooling into methylene chloride containing DMC added thereto, subsequently triethylamine is added dropwise thereto, and the resulting mixture is stirred at room temperature to effect alienation. Thus, the diastereomer mixture (III) of optically active allene-1,3-dimenthyl ester is obtained.

The diastereomer mixture is the mixture of (R)-allene-1,3-dimenthyl ester [(III)-R] and (S)-allene-1,3-dimenthyl ester [(III)-S], and the R- and S-enantiomers are in a rapid equilibrium relation in the presence of triethylamine. Therefore, when the diastereomer mixture (III), in a pentane solution and in the presence of a catalytic amount of triethylamine, is cooled to about −20∼−80° C. to effect asymmetric transformation with simultaneous crystallization of the R-enantiomer (crystallization-induced asymmetric transformation, hereinafter referred to as asymmetric crystallization), the equilibrium is shifted, and the (R)-allene compound alone separates out. In the above-mentioned example, (R)-allene-1,3-dimenthyl ester {(III)-R; [3R(1R, 2S,5R)]-bis[5-methyl-2-(1-methylethyl)cyclohexyl]-2,3-pentadienedioate} alone can be obtained in a high yield. In the same manner, when (+)-menthol is used as the optically active alcohol, (S)-allene-1,3-dimenthyl ester [(III)-S] alone can be obtained.

According to the method of the first step of the present invention, the diastereomer mixture (III) of allene-1,3-dimenthyl ester can be obtained only by conducting two stages of reaction, esterification and dehydration (alienation). On the other hand, according to the previous methods, for example four stages of reaction are necessary, that is, methyl acetone-dicarboxylate is subjected to chlorination with phosphorus pentachloride, then demethylation with hydrochloric acid, esterification with an optically active alcohol and thereafter dehydrochlorination. (Kanematsu K. et al., Tetrahedron Lett., 1992, 33, 5787–5790); thus, the preparation is complicated and troublesome.

According to the present method, moreover, an about 1:1 mixture of diastereomers is subjected, while being maintained in an equilibrium state by means of the presence of a tertiary amine, to conditions under which one of the diastereomers alone will separate out, whereby asymmetric crystallization is effected and a specific diastereomer can be selectively obtained from a diastereomer mixture without resorting to troublesome optical resolution. Thus, the present method is a very simple and highly efficient one.

In the present invention, the dehydrating agent used in the esterification of acetonedicarboxylic acid and the alienation of 1,3-acetonedicarboxylic acid menthyl ester is preferably an imidazolinium salt, such as 2-chloro-1,3-dimethylimidazolium chloride and 2-chloro-1,3-dimethylimidazolinium hexafluorophosphate. The basic substance used is preferably a tertiary amine having a high basicity, for example, trimethylamine, triethylamine, dimethylaminopyridine, N,N-diisopropyl-methylamine, N,N-diisopropylethylamine, pyrrolidine, (S)-2-methoxymethylpyrrolidine and sparteine.

It is as shown in Examples 1 and 2 that by using the above-mentioned imidezolinium salt as the dehydrating agent and the amine as the basic substance, the reactions of esterification and alienation respectively proceed in one stage, and hence the present method is useful for shortening the process steps and improving the yield. However, the allene-1,3-dicarboxylic acid esters obtained in Examples 1 and 2 are all racemate; thus, to obtain optically active compounds, it is preferable to obtain an optically active allene compound as the ester of an optically active alcohol and acetonedicarboxylic acid.

The optically active alcohols used for synthesizing the acetonedicarboxylic acid derivatives used in this step include, for example, the following compounds:

(−)-menthol, (+)-menthol, (+)-isomenthol, (+)-borneol, (−)-borneol, (S)-(−)-2-methyl-1-butanol, (S)-(+)-4-decanol, (S)-(+)-3-tridecanol, (S)-(+)-3-undecanol, (S)-(+)-4-tetradecanol, (S)-(−)-2-methyl-1-decanol, (S)-(−)-2-methyl-1-dodecanol, (R)-2,2,2-trifluoro-1-(9-anthryl)ethanol, (S)-2,2,2-trifluoro-1-(9-anthryl)ethanol, (−)-8-phenylmenthol, (S)-(−)-1-phenyl-ethanol, (1R,2S)-(−)-2-phenyl-1-cyclohexanol, (1R,2S)-(+)-2-phenyl-1-cyclohexanol, (R)-(+)-1-phenylethanol, (S)-(+)-pentyloxy-2-propanol, (S)-(+)-1-octyloxy-2-propanol, (R)-(−)-2-octanol, (S)-(+)-2-octanol, (R)-(−)-2-nonanol, (S)-(+)-2-nonanol, (R)-(+)-endo-5-norbornen-2-ol, (R)-(+)-endo-5-norborneol, (S)-(−)-2-methyl-1-octanol, (S)-(−)-methyl lactate, (R)-(+)-methyl lactate, (S)-(+)-methyl mandelate, (S)-(+)-methyl-3-hydroxy-2-methyl propionate, (R)-(−)-methyl-3-hydroxy-2-methyl propionate, (R)-(−) -methyl-2-hydroxypentanoate, (S)-(+)-methyl-3-hydroxypentanoate, methyl (R)-(−)-3-hydroxy-butyrate, methyl (S)-(+)-3-hydroxybutyrate, (R)-(−)-1,2-O-isopropylideneglycerol, (S)-(+)-1,2-O-isopropylidene-glycerol, (R)-4-hydroxypyrrolidone, (S)-4-hydroxy-pyrrolidone, (R)-2-hydroxy-1,2,2-triphenylethyl acetate, (S)-2-hydroxy-1,2,2-triphenylethyl acetate, (S)-2-hydroxy-2-phenylacetophenone, (R)-(−)-5-hydroxymethyl-2(5H)-furanone, (S)-(+)-hydroxymethyl-2(5H)-furanone, (R)-γ-hydroxymethyl-γ-butyrolactone, (S)-γ-hydroxymethyl-γ-butyrolactone, (S)-(+)-1-hexyloxy-2-propanol, (R)-(−)-2-heptanol, (S)-(+)-2-heptanol, (S)-(+)-1-heptyloxy-2-propanol, (R)-glycerol acetonide, (S)-glycerol acetonide, (R)-(+)-1-fluoro-2-octanol, (R)-1-fluoro-3-pentyloxy-2-propanol, (R)-1-fluoro-2-decanol, heptyloxy-2-propanol, (R)-1-fluoro-3-hexyloxy-2-propanol, (S)-(+)-2-ethyl-1-octanol, (R)-(−)-ethyl mandelate, (S)-(+)-ethyl mandelate, (R)-(+)-ethyl-4-chloro-3-hydroxybutanoate, (S)-(−)-ethyl-4-chloro-3-hydroxybutanoate, (R)-(−)-ethyl-3-hydroxybutanoate, (S)-(+)-2-dodecanol, (S)-(+)-4-dodecanol, (R)-diphenylprolinol, (S)-diphenylprolinol, (R)-di-2-naphthylprolinol, (S)-di-2-naphthylprolinol, (R)-(+)-dimethyl maleate, (S)-(−)-dimethyl maleate, (4S,5S)-(−)-4,5-dihydro-4-hydroxymethyl-2-methyl-5-phenyloxazole, (S)-(+)-6,6'-dibromo-1,1'-bi-2-naphthol, (S)-(+)-6,6'-dibromo-1,1'-bi-2-naphthol monomethyl ether, (R)-(−)-6,6'-dibromo-1,1'-bi-2-naphthol, (R)-(−)-6,6'-dibromo-1,1'-bi-2-naphthol monomethyl ether, (R)-(+)-4-chloro-3-hydroxybutyronitrile, (S)-(−)-4-chloro-3-hydroxybutyronitrile, (R)-(−)-3-chloromandelic acid ester, (R)-(+)-1-chloro-2-decanol, (S)-(−)-2-chloro-1-decanol, (R)-(+)-chloro-2-dodecanol, (S)-(−)-2-chloro-1-dodecanol, (R)-(−)-1-chloro-3-hexyloxy-2-propanol, (S)-(−)-3-butyn-2-ol, (S)-(+)-t-butyl-3-hydroxy-butanoate, (R)-(+)-1,1'-bi(2, 2'-naphthol), (R)-(+)-1,1'-bi(2,2'-naphthol)monomethyl ether, (S)-(−)-1,1'-bi(2,2'-naphthol) and (S)-(−)-1,1'-bi(2,2'-naphthol)monomethyl ether. Among the alcohols, those which have two functional groups, e.g., dialcohols and hydroxyacids, are preferably used after made into the form of monoalkyl ether or hydroxy acid ester by conventional methods to protect one of the functional groups.

The organic solvent used is not particularly restricted and may be those conventionally used in organic synthesis. Preferably used are pentane, hexane, methylene chloride, tetrahydrofuran etc. The esterification and the alienation are conducted at room temperature, and the transesterification is conducted under reflux. The asymmetric crystallization is carried out at a temperature range which is not higher than room temperature and in which crystallization takes place, which may be properly selected according to the system concerned.

The second step of the present invention is the step of obtaining an optically active. 7-azabicyclo-[2.2.1]heptane derivative by the Diels-Alder reaction of an optically active allene-1,3-dicarboxylic acid ester with a dienophile. One mode of the second step is described below with reference to the following formula (10), wherein R is a group derived from an optically active alcohol and Boc is the t-butoxycarbonyl group.

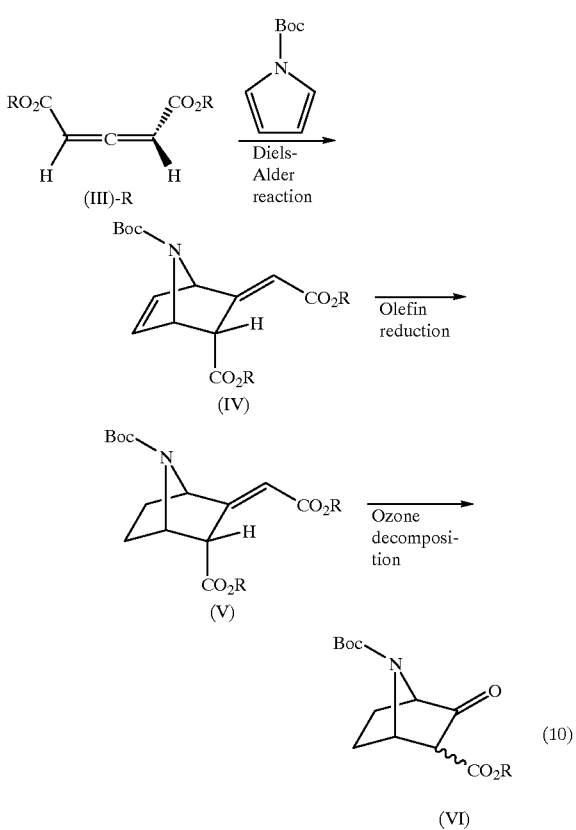

example, the benzyl group, methoxybenzyl group, nitrobenzyl group and chlorobenzyl group, and the tri-loweralkylsilyl group may be, for example, the trimethylsilyl group, triethylsilyl group and triphenylsilyl group.

The optically active 7-azabicyclo[2.2.1]heptene derivative (IV) {[1S,2R(1R,2S,5R),3Z(1R,2S,5R),4R]-5-methyl-2-(1-methylethyl)cyclohexyl 3-[2-[[5-methyl-2-(1-methylethyl)cyclohexyl]oxy]-2-oxoethylidene]-7-(t-butoxycarbonyl)-7-azabicyclo[2.2.1]hept-5-ene-2-carboxylate; R=(−)-menthylgroup} resulting from the Diels-Alder reaction is obtained stereoselectively only in the form of endo-adduct.

The optically active 7-azabicyclo[2.2.1]heptene derivative (IV) has two kinds of olefin, of which the isolated olefin can be selectively reduced. The reduction may be conducted by using a conventionally used reduction catalyst, such as Pt, Pd and Wilkinson complex, with hydrogen at about 10 atm. The reduction proceeds nearly quantitatively to give an optically active 7-azabicyclo[2.2.1]heptane derivative (V).

The derivative (V) is then subjected to ozone decomposition to obtain an optically active 7-aza-bicyclo[2.2.1]heptan-2-one-3-carboxylic acid ester (VI), a ketoester compound. The ozone decomposition is conducted by using methylene chloride as the solvent and passing ozone gas through the reaction solution at about −70 to −80° C., and the ozonide formed is decomposed with dimethyl sulfide or triphenylphosphine. As compared with a case of using methanol as a solvent, wherein the ketoester compound is difficult to obtain directly by ozone decomposition and it is necessary first to reduce the ester into an alcohol and then to subject the alcohol to ozone decomposition, the present method can attain the intended object with a one stage less reaction.

In the example described above the (−)-ketoester compound was obtained by using a material wherein R is the (−)-menthyl group, whereas when (+)-menthol is used, the (+)-ketoester compound, namely (+)-7-azabicyclo[2.2.1]heptan-2-one-carboxylic acid ester (VI), can be obtained.

The third step of the present invention is the step of synthesizing a halopyridyl-azacyclopentane derivative, e.g., (−)-epibatidine, by using as a precursor the optically active 7-azabicyclo[2.2.1]heptan-2-one-3-carboxylic acid ester (VI) obtained in the second step. One mode of this step is described below with reference to the following formula (11) [R=(−)-menthyl group].

The optically pure (R)-allene-1,3-dicarboxylic acid menthyl ester [(III)-R; R=(−)-menthyl group] obtained in the first step shown in the formula (9) is reacted with an N-acylpyrrole, e.g., N-t-butoxycarbonyl-pyrrole, as a dienophile. The Diels-Alder reaction proceeds both in the presence and in the absence of a Lewis acid, but gives a higher selectivity when conducted in the presence of a Lewis acid. The amount of the Lewis acid added may be a catalytic amount and is not more than 1.5 equivalents, preferably not more than 1.2 equivalents, relative to the allene compound. When a Lewis acid is absent, the reaction is carried out with heating under reflux in a solvent. The amount of pyrrole used is not particularly limited, but a higher yield can be obtained by using the excess thereof.

The dienophile favorably used is pyrrole, which is preferably used as a compound wherein the amino group is protected with a lower aliphatic acyl group, aromatic acyl group, formyl group, vinyl group, lower alkoxycarbonyl group, aralkylcarboxyl group, aryloxycarbonyl group, aryloxycarbonyl group, aralkyl group, tri-lower alkylsilyl group, and the like. The lower aliphatic acyl group used is a group of 1–6 carbon atoms, such as acetyl group, propionyl group, butyryl group, isobutyryl group, valeryl group, isovaleryl group and pivaloyl group. The aromatic acyl group may be, for example, the benzoyl group, toluoyl group, xyloyl group and phenylacetyl group, the lower alkoxycarbonyl group may be, for example, the methoxycarbonyl group, ethoxycarbonyl group, propoxycarbonyl group, butoxycarbonyl group and t-butoxycarbonyl group, the aralkyloxycarbonyl group may be, for example, the benzyloxycarbonyl group, methoxybenzylcarbonyl group and chlorobenzyloxycarbonyl group, the aryloxycarbonyl group may be, for example, the phenyloxycarbonyl group and nitrophenoxycarbonyl group, the aralkyl group may be, for

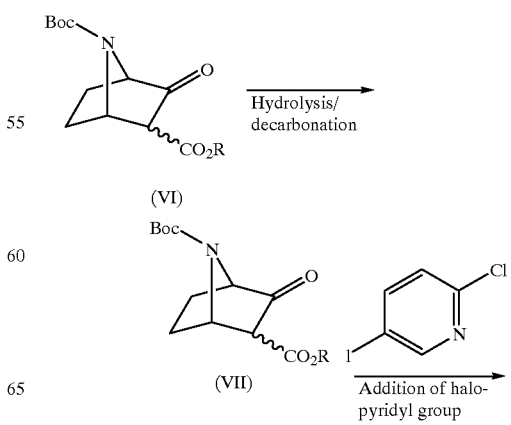

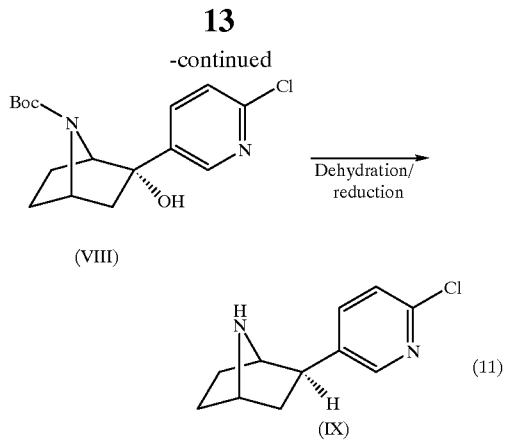

The 7azabicyclo[2.2.1]heptan-2one-carboxylic acid ester (VI) can be used for synthesis of epibatidine by using a known method (Fletcher et al., J. Org. Chem., 1994, 59, 1771–1778). Thus, the 7-azabicyclo[2.2.1]-heptan-2-one-3-carboxylic acid ester (VI) is subjected to simultaneous hydrolysis and decarbonation with an acid to obtain 7-azabicyclo[2.2.1]heptan-2-one (VII), to which is then added 2-chloro-5-iodopyridine in the presence of n-BuLi at −70° C., and the resulting addition product is then subjected to dehydration, reduction and deprotection of the amino group to obtain (−)-epibatidine (IX), which is one of the halopyridyl-azacyclopentane derivative and is a naturally obtainable optically active compound. This is also demonstrated from the fact that the angle of rotation $[\alpha]_D^{17}=-74.5$ and NMR data of (1R,4S)-7-(t-butoxycarbonyl)-7-azabicyclo[2.2.1]heptan-2-one (VII) obtained in Example 13 are in good agreement with the angle of rotation $[\alpha]_D^{17}=-72.6$ and NMR data reported for natural-type (1R,4S)-7-(t-butoxycarbonyl)-7-azabicyclo-[2.2.1]heptan-2-one (Rapoport, H. et al., J. Org. Chem., 1995, 60, 2683–2691).

The halopyridyl-azacyclopentane derivatives are represented by the formula (8) as described above and include, for example, exo-2-(6'-chloro-3'-pyridyl)-7-azabicyclo[2.2.1] heptane, exo-2-(6'-bromo-3'-pyridyl)-7-azabicyclo[2.2.1] heptane, exo-2-(6'-fluoro-3'-pyridyl)-7-azabicyclo[2.2.1] heptane, exo-2-(6'-chloro-2'-pyridyl)-7-azabicyclo[2.2.1] heptane, exo-2-(6'-chloro-4'-pyridyl)-7-azabicyclo[2.2.1] heptane, exo-2-(5'-chloro-3'-pyridyl)-7-azabicyclo[2.2.1] heptane, exo-2-(4'-bromo-3'-pyridyl)-7-azabicyclo[2.2.1] heptane, and exo-2-(2'-chloro-3'-pyridyl)-7-azabicyclo [2.2.1]heptane. The halogen attached to the pyridyl group may be the radioactive isomer thereof.

EXAMPLES

The present invention is described in detail below with reference to Examples, but the invention is in no way limited thereto.

The methods used for measuring the substances obtained and the solvents commonly used are as follows.

(1) Melting point: YANAGIMOTO melting point measuring apparatus was used.
(2) $H^1$-NMR: Determined with JEOL JMN-EX270, Varian XL-300 spectrometer. The chemical shift value was indicated by ppm, with tetramethylsilane (TMS) used as the internal standard.
(3) Angle of rotation: Determined by using Horiba Sepa-200.
(4) Infrared spectra: Determined with Jasco IR-810, SHIMADZU FTIR-8300. The wave number was indicated by $cm^{-1}$.
(5) Mass spectra: Determined with JEOL JMX-SX102AQQ mass spectrometer and JEOL JMS-Gcmate mass spectrometer.
(6) Elementary analysis: Determined with PERKINELMER Series CHNS/O Analyzer 2400.
(7) Column for column chromatography: Wakogel C-200 (Wako Pure Chemical Industries, Ltd.), Wakogel C-300 (Wako Pure Chemical Industries, Ltd.) and Kieselgel 60 Art. 9385 (Merck) were used.
(8) Preparative TLC column: Kieselgel 60 $F_{254}$ Art. 5715 (Merck) and Kieselgel 60 $F_{254}$ Art. 5744 (Merck) were used.
(9) Preparative HPLC: JAI LC-908 was used; columns used were JAIGEL-1H and JAIGEL-2H.
(10) The ethereal solvents and the aromatic solvents employed for reaction were distilled from sodium-benzophenone ketyl before use. Methylene chlorine used was washed 10 times with water to remove methanol, the stabilizer, and distilled from $CaH_2$ before use. Other anhydrous solvents used were made anhydrous by conventional methods. The NaH employed for reaction was used after freed from oily substances by washing 3 times with ether.

Example 1

Synthesis of allene-1,3-dicarboxylate Using DMC

Under nitrogen gas stream, 100 ml of dry methylene chloride was added to 5.80 g (34.5 mmol) of a dehydrating agent DMC, and 5.00 g (28.7 mmol) of dimethyl-1,3-acetonedicarboxylate was added dropwise to the resulting DMC solution with ice cooling, then 11.6 g (115 mmol, 4 equivalents relative to dimethyl-1,3-acetonedicarboxylate) of triethylamine ($Et_3N$) was added dropwise thereto, and the resulting mixture was stirred at room temperature for one hour. After completion of the reaction, the reaction mixture was purified by column chromatography on silica gel, whereby 4.05 g of dimethyl-1,3-acetonedicarboxylate was obtained. Yield 90%.

Yellow oil; $H^1$-NMR(CDCl$_3$, 270 MHz) δ: 6.06 (s, 2H), 3.78 (s, 6H); IR (CHCl$_3$): 3036, 2955, 2359, 1967, 1720, 1439, 1269 $cm^{-1}$; EI-MS m/z 156 (M$^+$, 7), 128 (100), 112 (23), 98 (3); HRMS 156.0422: $C_7H_8O_4$(M$^+$) 156.0420

Reactions were carried out in the same manner as above wherein, while the amount of DMC used was fixed at 1.2 equivalents, the amount of $Et_3N$ used was varied in the range from 1 to 3 equivalents relative to dimethyl-1,3-acetonedicarboxylate and the ester group was changed to the methyl group, ethyl group, benzyl group and t-butyl group. The results obtained are shown in Table 1. The yields were shown for the compounds (A) and (B) of the following formula (12).

It can be seen that when the amount of $Et_3N$ used is less than 3 equivalents relative to the 1,3-acetonedicarboxylic acid ester, vinyl chloride (B) is formed as a by-product, whereas when it is 3 equivalents or more, allene compounds alone can be obtained in a yield not lower than 70%.

TABLE 1

| No. | R | R$^1$ | Et$_3$N equivalent | Time (Hr) | Yield (A) (%) | Yield (B) (%) |
|---|---|---|---|---|---|---|
| 1 | Me | H | 1 | 24 | — | 44 |
| 2 | Me | H | 2 | 22 | 72 | 21 |
| 3 | Me | H | 3 | 1 | 90 | — |
| 4 | Me | Me | 3 | 2 | 73 | — |
| 5 | Et | H | 3 | 0.5 | 92 | — |
| 6 | Bn | H | 3 | 2.5 | 70 | — |
| 7 | t-Bu | H | 3 | 0.5 | 71 | — |

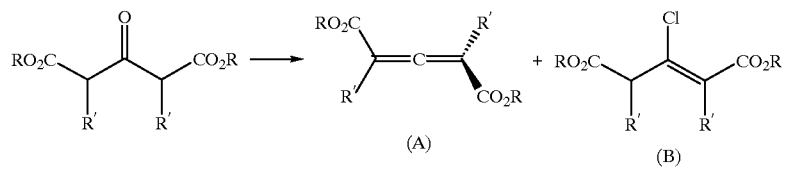

(12)

Example 2

Synthesis of allene-1,3-dicarboxylate Using Various Bases

In the reaction of transforming acetone-dicarboxylic acid esters into allene-1,3-dicarboxylates shown in the formula (12), the behavior of the reaction was studied by using various amines in place of triethylamine. By using dimethyl 1,3-acetone-dicarboxylate as the reaction substrate and using 1.2 equivalents of DMC and 3 equivalents of various amines, allene compounds were synthesized in methylene chloride at room temperature. The results obtained are shown in Table 2 below.

When pyridine, which is weaker in basicity than triethylamine, was used, the reaction did not proceed but with other amines listed the present reactions all proceeded to give allene compounds (A). Even when an optically active amine, (S)-2-methoxymethylpyrrolidine or sparteine, was used, racemate was formed and an optically active allene compound could not be obtained.

TABLE 2

| No. | Base | Time (Hr) | Yield (%) (A) | Yield (%) (B) |
|---|---|---|---|---|
| 1 | Triethylamine | 1 | 90 | — |
| 2 | N,N-Diisopropylethyl-amine | 1.5 | 84 | 8 |
| 3 | Pyridine | 15 | n.r. | n.r. |
| 4 | (S)-2-Methoxymethyl-pyrrolidine | 0.5 | 61 | 23 |
| 5 | Sparteine | 1 | 78 | — |

Example 3

Synthesis of 1R,2S,5R-bis[5-methyl-2-(1-methylethyl)cyclohexyl]-1,3-acetonedicarboxylate By using (−)-menthol, optically active acetonedicarboxylic acid menthyl ester was synthesized. Under nitrogen gas stream, 5.00 g (34.2 mmol) of acetonedicarboxylic acid and 10.7 g (68.4 mmol) of (−)-menthol were added to a solution of 12.7 g (75.3 mmol) of DMC in 50 ml dry methylene chloride, then 10.8 g (137 mmol) of pyridine was added dropwise thereto in a water bath and the resulting mixture was stirred at room temperature for 7.5 hours. After completion of the reaction, the deposited solid was filtered with celite, and the crude product obtained was purified by silica gel column chromatography (AcOEt: hexane=1:20) to obtain 6.48 g of 1R,2S,5R-bis[5-methyl-2-(1-methylethyl)-cyclohexyl]-1,3-acetonedicarboxylate. Yield 45%.

Pale yellow oil; H$^1$-NMR(CDCl$_3$, 300 MHz) δ: 4.80–4.68 (m, 2H), 3.58 (d, J=5.9 Hz, 4H), 2.05–1.99 (m, 2H), 1.89–1.84 (m, 2H), 1.70–1.65 (m, 4H), 1.59–0.75 (m, 28H); IR (CHCl$_3$): 2961, 2930, 1724, 1653, 1456, 1244, 1180 cm$^{-1}$; FAB-MS m/z 423 [M+H]$^+$; HRMS 423.3110: C$_{25}$H$_{43}$O$_5$ [M+H]$^+$ 423.3119

Example 4

Synthesis of diastereomer mixture of [3R(1R,2S, 5R)]-bis[5-methyl-2-(1-methylethyl)cyclohexyl]-2,3-pentadienedioate and [3S(1R,2S,5R)]-bis(5-methyl-2(1-methylethyl)cyclohexyl]-2,3-pentadienedioate Under nitrogen gas stream, 100 ml of dry methylene chloride was added to 5.80 g (34.5 mmol) of a dehydrating agent DMC, and 100 mg (0.350 mmol) of the 1R,2S,5R-bis[5-methyl-2-(1-methylethyl)cyclohexyl]-1,3-acetonedicarboxylate synthesized in Example 3 was added dropwise with ice cooling to the resulting MDC solution, then 11.6 g (115 mmol) of Et$_3$N was added dropwise thereto, and the resulting mixture was stirred at room temperature for 0.5 hour, to obtain 82.7 mg of a diastereomer mixture of optically active allenedicarboxylic acid dimenthyl ester in 86% yield.

Yellow oil; H$^1$-NMR (CDCl$_3$, 270 MHz) δ: 6.01 (s, 1.1H), 5.99 (s, 0.9H), 4.75 (dt, J=10.8, 4.4 Hz, 2H), 2.03 (br.d, J=11.9 Hz, 2H), 1.87, 1.84 (qd, J=6.9, 2.6 Hz, total 6H), 1.77–1.63 (m, 4H), 1.63–1.34 (m, 6H), 1.18–0.91 (m, 16H), 0.78, 0.77 (d, J=6.9 Hz, total 6H); IR (CHCl$_3$): 1945, 1685 cm$^{-1}$; FAB-MS m/z 405 [M+H]$^+$; HRMS 405.3005: C$_{25}$H$_{41}$O$_4$[M+H]$^+$ 405.3013

Example 5

Asymmetrization Reaction of Diastereomer Mixture; Synthesis of [3R(1R,2S,5R)]-bis[5-methyl-2-(1-methylethyl)cyclohexyl]-2,3-pentadienedioate Crystallization-induced asymmetric transformation (asymmetric crystallization) of a diastereomer mixture was conducted.

To 5 ml of a pentane solution of 2 g (4.95 mmol) of the diastereomer mixture (R:S=4:5) obtained in Example 4 was added 5.00 mg (0.05 mmol) of Et$_3$N, and the resulting mixture was placed in a refrigeration chamber and allowed to stand for one day while being kept at −20° C. After large grains of crystals had been deposited, the mixture was further allowed to stand for one day at −78° C. After small grains of crystals had been deposited, the mother liquor was removed with a pipette at −78° C., care being taken so that the crystals might not be sucked up. The crystals were washed 4–5 times with a small amount of cooled pentane, and the solvent remaining in crystals was evaporated in vacuo. The mother liquor removed above was further subjected to the same operation repeatedly two times. Thus, 1.8 g of crystals was obtained. The crystals obtained were only of the R-enantiomer. Yield was 90%.

Colorless crystal; mp: 83° C.; $[\alpha]_D^{17}$: −240.1 (c=1.1, CHCl$_3$); H$^1$-NMR(CDCl$_3$, 300 MHz) δ: 5.99 (s, 2H), 4.75 (dt, J=10.8, 4.4 Hz, 2H), 2.03 (br.d, J=11.9 Hz, 2H), 1.87, 1.84 (qd, J=6.9, 2.6 Hz, total 6H), 1.77–1.63 (m, 4H), 1.63–1.34 (m, 6H), 1.18–0.91 (m, 16H), 0.78, 0.77 (d, J=6.9 Hz, total 6H); IR (CHCl$_3$): 1945, 1685 cm$^{-1}$; FAB-MS m/z 405[M+H]$^+$; HRMS 405.3005: C$_{25}$H$_{41}$O$_4$[M+H]$^+$ 405.3013

Example 6

Diels-Alder Reaction of allene-1,3-dicarboxylic Acid Derivative with Pyrrole Derivative By using allene-1,3-dicarboxylic acid methyl ester as the allene compound, the Diels-Alder reaction thereof with a pyrrole derivative was conducted under various conditions. Method 1: Under nitrogen gas stream, 224 mg (1.68 mmol) of AlCl$_3$ was added to 25 ml of a dry methylene chloride solution of 620 mg (1.53 mmol) of allene-1,3-dicarboxylic acid methyl ester at −78° C., the resulting mixture was stirred for 30 minutes, then N-butoxycarbonylpyrrole was added dropwise thereto and the mixture was stirred at −78° C. for 13 hours. After completion of the reaction, the reaction liquid was poured into water, then extracted with chloroform, the extract was dried with Na$_2$SO$_4$, filtrated and the solvent was evaporated in vacuo. The crude product thus obtained was purified by silica gel chromatography (AcOEt:hexane= 1:4) to obtain 681 mg of methyl 3-(2-methoxy-2-oxoethylidene)-7-(t-butoxycarbonyl)-7-azabicyclo[2.2.1]hept-5-ene-2-carboxylate. Yield 73%.

Method 2: Under nitrogen gas stream, 1.10 g (6.40 mmol) of N-butoxycarbonylpyrrole was added dropwise to a solution of 100 mg (0.64 mmol) of allene-1,3-dicarboxylic acid methyl ester in 10 ml of a dry methylene chloride, and the resulting mixture was stirred for 24 hours with heating at 90° C. After completion of the reaction, the solvent was evaporated in vacuo, and the resulting crude product was purified by silica gel chromatography to obtain 184 mg of methyl 3-(2-methoxy-2-oxoethylidene)-7-(t-butoxycarbonyl)-7-azabicyclo[2.2.1]hept-5-ene-2-carboxylate. Yield 89%.

Yellow oil; H$^1$-NMR(CDCl$_3$, 300 MHz) δ: 6.24–6.30 (m, 2H), 6.07 (d, J=1.7 Hz, 1H), 5.1–4.98 (m, 2H), 3.99 (s, 1H), 3.68 (s, 3H), 3.67 (s, 3H), 1.41 (s, 9H); IR (CHCl$_3$): 3032, 3013, 2934, 1711, 1369, 1231, 1167 cm$^{-1}$; FAB-MS m/z 324[M+H]$^+$; HRMS 324.1447: C$_{16}$H$_{22}$O$_6$N[M+H]$^+$ 324.1459

The results of experiments made under varied conditions are shown in Table 3 below.

Experiment Nos. 1–4 were conducted by the method 1, and the amount of Lewis acid used was 1.2 equivalents in each of the experiments. Experiment Nos. 5–7 were conducted by the method 2 wherein heating at 90° C. under reflux in toluene was adopted. Through all of the experiments, the use of pyrrole in excess improves the yield, whereas the use of a Lewis acid gives a better selectivity.

TABLE 3

| No. | Dienophile equivalent | Lewis | Solvent | Temp. (° C.) | Yield (%) |
|---|---|---|---|---|---|
| 1 | 2 | AlCl$_3$ | CH$_2$Cl$_2$ | −78 → 0 | 30 |
| 2 | 2 | AlCl$_3$ | CH$_2$Cl$_2$ | −78 | 41 |
| 3 | 2 | Sc(CF$_3$SO$_3$)$_3$ | CH$_2$Cl$_2$ | −78 | 47 |
| 4 | 10 | AlCl$_3$ | CH$_2$Cl$_2$ | −78 | 73 |
| 5 | 1 | — | Toluene | 90 | 43 |
| 6 | 2 | — | Toluene | 90 | 68 |
| 7 | 10 | — | Toluene | 90 | 89 |

Example 7

Synthesis of [1S,2R(1R,2S,5R),3Z-(1R,2S,5R),4R]-5-methyl-2-(1-methylethyl)cyclohexyl 3-[2-[[5-methyl-2-(1-methylethyl)cyclohexyl]oxy]-2-oxoethylidene]-7-(t-butoxycarbonyl)-7-azabicyclo[2.2.1]-hept-5-ene-2-carboxylate By using 880 mg (2.20 mmol) of the optically active (R)-allenecarboxylic acid menthyl ester synthesized in Example 5, according to a similar procedure to that in the synthesis example by means of a Diels-Alder reaction using AlCl$_3$ shown in Example 6 (method 1), with 9 hours of stirring, 1.08 g of an optically active compound (IV) shown in the formula (10), [1S,2R(1R,2S,5R),3Z(1R,2S,5R),4R]-5-methyl-2-(1-methylethyl)cyclohexyl 3-[2-[[5-methyl-2-(1-metnylethyl)-cyclohexyl]oxy]-2-oxoethylidene]-7-(t-butoxycarbonyl)-7-azabicyclo[2.2.1]hept-5-ene-2-carboxylate (R=(−)-menthyl group), was obtained. Yield 86%. Colorless crystal; mp: 140–142.7° C.; $[\alpha]_D^{17}$: −3.2 (c=0.68, CHCl$_3$); H$^1$-NMR(CDCl$_3$, 300 MHz) δ: 6.42–6.30 (m, 2H), 6.04 (d, J=1.7 Hz, 1H), 5.02–4.80 (m, 2H), 4.61 (ddd, J=10.8, 10.8, 4.3 Hz, 1H), 4.55 (dt, J=10.8, 4.4 Hz, 1H), 4.06 (s, 1H), 2.05–1.84 (m, 4H), 1.41 (s, 9H), 1.68–0.69 (m, 34H); IR(CHCl$_3$): 2958, 2930, 1705, 1369, 1175 cm$^{-1}$; FAB-MS m/z 572(M+H)$^+$; HRMS 572.3951: C$_{14}$H$_{54}$O$_6$N[M+H]$^+$ 572.3955

Example 8

Reduction of Isolated Olefin; Synthesis of exo-methyl-2-(2-methoxy-2-oxoethylidene)-7-(t-butoxycarbonyl)-7-azabicyclo[2.2.1]heptane-3-carboxylate and endo-methyl-2-(2-methoxy-2-oxoethylidene)-7-(t-butoxycarbonyl)-7-azabicyclo[2.2.1]heptane-3-carboxylate To a solution of 4.90 g (15.2 mmol) of the compound synthesized in Example 6, methyl-2-(2-methoxy-2-oxoethylidene)-7-(t-butoxycarbonyl)-7-azabicyclo[2.2.1]hept-5-ene-3-carboxylate in 15 ml methanol, was added 140 mg (0.15 mmol) of Wilkinson complex, [(C$_6$H$_5$)$_3$P]$_3$RhCl, and the resulting mixture was stirred under an inert atmosphere of hydrogen at 10 atm. for 15 hours. After completion of the reaction, metallic Rh was removed by celite filtration, the filtrate was concentrated in vacuo, and the resulting crude product was purified by silica gel chromatography (AcOEt:hexane=1:5) to obtain 2.69 g (55% yield) of the exo-adduct and 2.24 g (45% yield) of the endo-adduct.

exo-adduct: pale yellow oil; H$^1$-NMR(CDCl$_3$, 300 MHz) δ: 6.00 (s, 1H), 4.82–4.49 (m, 2H), 3.69 (s, 1H), 3.67 (s, 6H), 2.05–1.95 (m, 2H), 1.60–1.45 (m, 2H), 1.43 (s, 9H); IR (CHCl$_3$): 3030, 3013, 2983, 1734, 1699, 1367, 1229, 1163 cm$^{-1}$; FAB-MS m/z 326[M+H]$^+$; HRMS 326.1604: C$_{16}$H$_{24}$O$_6$N[M+H]$^+$ 326.1618 endo-adduct: pale yellow oil; H$^1$-NMR (CDCl$_3$, 300 MHZ) δ: 5.92 (d, J=2.5 Hz, 1H), 4.59 (d, J=4.9 Hz, 1H), 4.53 (t, J=4.4 Hz, 1H), 1.81–1.58 (m, 3H), 1.43 (s, 9H); IR (CHCl$_3$): 3030, 3013, 2953, 1701, 1367, 1231, 1163 cm$^{-1}$; FAB-MS m/z 326[M+H]$^+$; HRMS 326.1604: C$_{16}$H$_{24}$O$_6$N[M+H]$^+$ 326.1618

Example 9

Synthesis of [1S,2R(1R,2S,5R),3Z-(1R,2S,5R),4R]-5-methyl-2-(1-methylethyl)cyclohexyl 3-[2-[[5-methyl-2-(1-methylethyl)cyclohexyl]oxy]-2-oxoethylidene]-7-(t-butoxycarbonyl)-7-azabicyclo[2.2.1]-heptane-2-carboxylate To a solution of 578 mg (1.01 mmol) of the optically active compound obtained in Example 7, [1S,2R(1R,2S,5R), 3Z(1R,2S,5R),4R]-5-methyl-2-(1-methylethyl)cyclohexyl 3-[2-[[5-methyl-2-(1-methylethyl)cyclohexyl]oxy]-2-oxoethylidene]-7-(t-butoxycarbonyl)-7-azabicyclo[2.2.1] hept-5-ene-2-carboxylate in 15 ml ethyl acetate, was added 10 mg of 10% Pd—C, and the resulting mixture was stirred under an inert atmosphere of hydrogen at 10 atm. for 5 hours. After completion of the reaction, metallic Pd was removed by celite filtration, the filtrate was concentrated in vacuo, and the resulting crude product was purified by PTLC (AcOEt:hexane=1:10) to obtain 573 mg of the objective product. Yield 99%.

White powder; mp: 152.0–152.6° C.; [α]$_D^{17}$: −75.1 (c=1.2, CHCl$_3$); H$^1$-NMR (CDCl$_3$, 300 MHz) δ: 5.88 (d, J=2.6 Hz, 1H), 4.63 (tt, J=10.6, 4.2 Hz, 2H), 4.54–4.50 (m, 2H), 4.00–3.99 (m, 1H), 2.15–1.49 (m, 10H), 1.43 (s, 9H), 1.41–0.87 (m, 24H), 0.77, 0.72 (d, J=6.9 Hz, total 6H); IR (CHCl$_3$): 2959, 2872, 1701, 1369, 1161 cm$^{-1}$; FAB-MS m/z 572[M+H]$^+$; HRMS 574.4106: C$_{34}$H$_{56}$O$_6$N[M+H]$^+$ 574.4135

Example 10

Synthesis of 7-(t-butoxycarbonyl)-3-methoxycarbonyl-7-azabicyclo[2.2.1]heptan-2-one Ozone gas was bubbled through a solution of 90 mg (0.28 mmol) of the endo-adduct obtained in Example 8, endo-methyl-2-(2-methoxy-2-oxoethylidene)-7-(t-butoxycarbonyl)-7-azabicyclo[2.2.1]heptane-3-carboxylate, in 15 ml methylene chloride, at −78° C. After confirming that the reaction solution had turned blue, ozone gas was bubbled for 1.5 hours. Then oxygen and nitrogen were bubbled through the solution to remove excess ozone gas, thereafter 86 mg (1.38 mmol) of Me$_2$S was added dropwise thereto, and the resulting mixture was stirred at room temperature for 14 hours. After completion of the reaction, the solvent was removed and the resulting crude product was purified by silica gel chromatography (AcOEt:hexane=1:2) to obtain 56.0 mg of the objective product as a diastereomer mixture of oxo-adduct:endo-adduct=1:1. Yield 74%.

Colorless oil; H$^1$-NMR(CDCl$_3$, 300 MHz) δ: 4.85 (d, J=4.9 Hz, 0.5H), 4.74 (dd, J=5.1, 4.1 Hz, 0.5H), 4.37 (d, J=4.3 Hz, 0.5H), 4.33 (d, J=5.1 Hz, 0.5H), 3.76 (s, 3×0.5H), 3.74 (s, 3×0.5H), 3.46 (d, J=5.1 Hz, 0.5H), 3.01 (s, 0.5H), 2.09–2.00 (m, 2H), 1.73–1.64 (m, 2H), 1.64 (s, 9H); IR (CHCl$_3$): 2984, 2959, 1778, 1734, 1701, 1369, 1159, 1103 cm$^{-1}$; FAB-MS m/z 270[M+H]$^+$;HRMS 270.1342: C$_{13}$H$_{20}$O$_5$N[M+H]$^+$ 270.1349

Example 11

Synthesis of [1S,2R(1R,2S,5R),3Z-(1R,2S,5R),4R]-5-methyl-2-(1-methylethyl)cyclohexyl 7-(t-butoxycarbonyl]-3-oxo-7-azabicyclo[2.2.1]heptane-2-carboxylate Ozone gas was bubbled through a solution of 100 mg (0.170 mmol) of the optically active compound obtained in Example 9, [1S,2R(1R,2S,5R),3Z(1R,2S,5R),4R]-5-methyl-2-(1-methylethyl)cyclohexyl 3-[2-[[5-methyl-2-(1-methylethyl)cyclohexyl]oxy]-2-oxoethylidene]-7-(t-butoxycarbonyl)-7-azabicyclo[2.2.1]heptane-2-carboxylate, in 20 ml methylene chloride, at −78° C. After confirming that the reaction solution had turned blue, ozone gas was bubbled for 30 minutes. Then O$_2$ and N$_2$ were bubbled through the solution to remove excess ozone, thereafter 137 mg (0.520 mmol) of Ph$_3$P was added thereto, and the resulting mixture was stirred at room temperature for 12 hours. After completion of the reaction the solvent was evaporated in vacuo, and the resulting crude product was purified by silica gel chromatography (AcOEt:hexane=1:5) to obtain the intended substance as a diastereomer mixture of oxo-adduct:endo-adduct=1:1.

Pale yellow oil; [α]$_D^{16}$: −70.9 (c=0.92, CHCl$_3$); H$^1$-NMR (CDCl$_3$, 300 MHz) δ: 4.85–4.84 (m, 0.5H), 4.77–4.68 (m, 2×0.5H), 4.38–4.37 (m, 0.5H), 4.31 (d, J=5.6 Hz, 0.5H), 3.43 (d, J=5.2 Hz, 0.5H), 2.97 (s, 0.5H), 2.05–1.88 (m, 6H), 1.73–1.63 (m, 5H), 1.52–1.43 (m, 1.5H), 1.46 (s, 9H), 1.26–0.88 (m, 7H), 0.75 (d, J=6.8 Hz, 3H); IR (CHCl$_3$): 2959, 1778, 1717, 1701, 1369, 1221, 1161 cm$^{-1}$; FAB-MS m/z 394[M+H]$^+$; HRMS 394.2594: C$_{22}$H$_{36}$O$_5$N[M+H]$^+$ 394.2607

Example 12

Synthesis of 7-(t-butoxycarbonyl)-7-azabicyclo [2.2.1]heptan-2-one

To 180 mg (0.970 mmol) of the diastereomer mixture obtained in Example 10, 7-(t-butoxycarbonyl)-3-methoxycarbonyl-7-azabicyclo[2.2.1]heptan-2-one, was added 3 ml of 10% HCl and the resulting mixture was heated under reflux at 100° C. for 3.5 hours. After completion of the reaction the solvent was evaporated in vacuo and the remaining water was removed by azeotropic distillation with ethanol. The crude product obtained was dissolved with 10 ml of dry methylene chloride, 169 ml (1.68 mmol) of Et$_3$N and 292 mg (1.34 mmol) of (Boc)$_2$O were added to the solution and the resulting mixture was stirred at room temperature for 12 hours. After completion of the reaction, the reaction mixture was poured into a saturated aqueous sodium chloride solution, then extracted with chloroform, the extract was dried with Na$_2$SO$_4$, then filtrated and the solvent was evaporated in vacuo. The crude product thus obtained was purified by silica gel chromatography (AcOEt:hexane=1:3) to obtain 91.0 mg of 7-(t-butoxycarbonyl)-7-azabicyclo[2.2.1]heptan-2-one. Yield 64%.

Colorless oil (solidifies on standing); mp: 60–62° C.; H$^1$-NMR (CDCl$_3$, 300 MHz) δ: 4.55 (t, J=4.5 Hz, 1H), 4.24 (d, J=4.9 Hz, 1H), 2.50–2.43 (m, 1H), 2.09–1.51 (m, 5H), 1.53 (s, 9H); IR (CHCl$_3$): 1760, 1690 cm$^{-1}$; FAB-MS m/z 212[M+H]$^+$; HRMS 212.1287: C$_{11}$H$_{18}$O$_3$N[M+H]$^+$ 212.1297

Example 13

Synthesis of (1R,4S)-7-(t-butoxycarbonyl)-7-azabicyclo[2.2.1]heptan-2-one

To 100 mg (0.250 mmol) of the optically active compound obtained in Example 11, [1S,2R(1R,2S,5R),3Z-(1R, 2S,5R),4R]-5-methyl-2-(1-methylethyl)cyclohexyl 7-(t-butoxycarbonyl)-3-oxo-7-azabicyclo[2.2.1]heptane-2-carboxylate was added 3 ml of an aqueous 10% HCl solution and the resulting mixture was stirred with heating at 100° C. under reflux for 3.5 hours. After completion of the reaction, the solvent was removed and the remaining water was removed by azeotropic distillation with ethanol. The crude product thus obtained was dissolved with 10 ml of dry methylene chloride, 77 ml (0.760 ml) of $Et_3N$ and 111 mg (0.51 mmol) of $(Boc)_2O$ were added to the solution, and the resulting mixture was stirred at room temperature for 12 hours. After completion of the reaction, the reaction mixture was poured into a saturated sodium chloride solution, then extracted with chloroform, the extract was dried with $Na_2SO_4$, filtered and the solvent was evaporated in vacuo. The crude product thus obtained was purified by silica gel chromatography (AcOEt:hexane=1:4) to obtain 29 mg of the objective substance. Yield 55%.

Colorless oil (solidifies on standing); mp: 60–62° C.; $[\alpha]_D^{17}$: −74.5 (c=1.0, $CHCl_3$); $H^1$-HMR ($CDCl_3$, 300 MHz) δ: 4.55 (t, J=4.5 Hz, 1H), 4.24 (d, J=4.9 Hz, 1H), 2.50–2.43 (m, 1H), 2.09–1.51 (m, 5H), 1.53 (s, 9H); IR ($CHCl_3$): 1760, 1690 $cm^{-1}$; FAB-MS m/z 212[M+H]$^+$; HRMS 212.1287: $C_{11}H_{18}O_3N[M+H]^+$ 212.1297.

What is claimed is:

1. A method for synthesis of an optically active halopyridyl-azacyclopentane derivative which consists of a first step of allowing an acetonedicarboxylic acid ester derivative of an optically active alcohol to react in the presence of a basic substance and a dehydrating agent to obtain a diastereomer mixture of an allene-1,3-dicarboxylic acid ester derivative and then subjecting the diastereomer mixture to asymmetric transformation to obtain an optically active (R)- or (S)-allene-1,3-dicarboxylic acid ester derivative, a second step of subjecting the optically active allene-1,3-dicarboxylic acid ester derivative to a Diels-Alder reaction, in the presence of a Lewis acid, with a dienophile to obtain an optically active 7-azabicyclo[2.2.1]heptene derivative and then reducing the optically active 7-azabicyclo[2.2.1]heptene derivative to obtain an optically active 7-azabicyclo[2.2.1]heptane derivative and a third step of preparing an optically active halopyridyl-azacyclopentane derivative from the optically active 7-azabicyclo[2.2.1]-heptane derivative.

2. The method for synthesis of an optically active halopyridyl-azacyclopentane derivative according to claim 1, wherein the acetonedicarboxylic acid ester derivative of an optically active alcohol is represented by the formula (1)

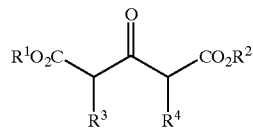

(1)

wherein $R^1$ and $R^2$ are each a group derived from an optically active alcohol and $R^3$ and $R^4$ are each a member selected from the group consisting of a hydrogen atom, alkyl group and aryl group, which may be the same or different from each other, the optically active allene-1,3-dicarboxylic acid ester derivative is the R- or S-enantiomer represented by the formula (2)

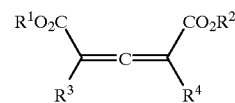

(2)

wherein $R^1$ and $R^2$ are each a group derived from an optically active alcohol and $R^3$ and $R^4$ are each a member selected from the group consisting of a hydrogen atom, alkyl group and aryl group, which may be the same or different from each other, the optically active 7-azabicyclo[2.2.1]heptene derivative is represented by the formula (3), or its enantiomer represented by formula (4)

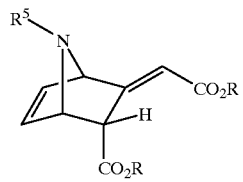

(3)

wherein $R^1$ and $R^2$ are each a group derived from an optically active alcohol and $R^5$ is a protective group for an amino group,

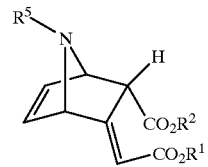

(4)

wherein $R^1$ and $R^2$ are each a group derived from an optically active alcohol and $R^5$ is a protective group for an amino group, the optically active 7-azabicyclo[2.2.1]heptane derivative is a ketoester compound represented by the formula (5), or its enantiomer represented by formula (6)

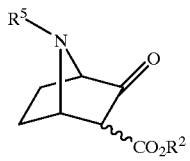

(5)

wherein $R^2$ is a group derived from an optically active alcohol and $R^5$ is a protective group for an amino group,

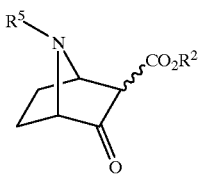
(6)

wherein $R^2$ is a group derived from an optically active alcohol and $R^5$ is a protective group for an amino group, or is an optically active ketone compound represented by the formula (7), or its enantiomer represented by formula (7)'

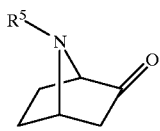
(7)

wherein $R^5$ is a protective group for an amino group,

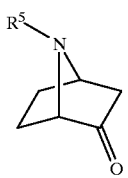
(7)' wherein $R^5$ is a protective group for an amino group, and the optically active halopyridyl-azacyclopentane derivative is represented by the formula (8), or its enantiomer represented by formula (8)'

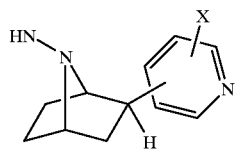
(8)

wherein X is a halogen atom selected from Cl, F, Br and I or a radioactive isomer thereof,

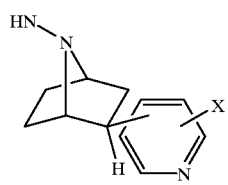
(8)' wherein X is a halogen atom selected from Cl, F, Br and I or a radioactive isomer thereof.

3. The method for synthesis of an optically active halopyridyl-azacyclopentane derivative according to claim 1 or 2, wherein the optically active alcohol is a member selected from the group consisting of (−)-menthol, (+)-menthol, (+)-isomenthol, (−)-8-phenylmenthol, (S)-(+)-6,6'-dibromo-1,1'-bi-2-naphthol, (S)-(+)-6,6'-dibromo-1,1'-bi-2-naphthol monomethyl ether, (R)-(−)-6,6'-dibromo-1,1'-bi-2-naphthol, (R)-(−)-6,6'-dibromo-1,1'-bi-2-naphthol monomethyl ether, (R)-(+)-1,1'-bi(2,2'-naphthol), (R)-(+)-1,1'-bi(2,2'-naphthol)monomethyl ether, (S)-(−)-1,1'-bi(2,2'-naphthol) and (S)-(−)-1,1'-bi(2,2'-naphthol)monomethyl ether.

4. The method for synthesis of an optically active halopyridyl-azacyclopentane derivative according to claim 1 or 2, wherein the dehydrating agent is 2-chloro-1,3-dimethylimidazolium chloride or 2-chloro-1,3-dimethylimidazolinium hexafluorophosphate.

5. The method for synthesis of an optically active halopyridyl-azacyclopentane derivative according to claim 1 or 2, wherein the basic substance is a tertiary amine.

6. The method for synthesis of an optically active halopyridyl-azacyclopentane derivative according to claim 3, wherein the dehydrating agent is 2-chloro-1,3-dimethylimidazolium chloride or 2-chloro-1,3-dimethylimidazolinium hexafluorophosphate.

7. The method for synthesis of an optically active halopyridyl-azacyclopentane derivative according to claim 3, wherein the basic substance is a tertiary amine.

8. A method for synthesis of an optically active allene-1,3-dicarboxylic acid ester derivative which consists of subjecting an acetonedicarboxylic acid and an optically active alcohol to esterification in the presence of a basic substance and a dehydrating agent, or subjecting an acetonedicarboxylic acid ester (wherein the ester group is a lower alkyl or phenyl group) and an optically active alcohol to transesterification in the presence of a basic substance, to obtain an optically active acetonedicarboxylic acid ester derivative, then subjecting the optically active acetonedicarboxylic acid ester derivative to a reaction in the presence of a basic substance and a dehydrating agent to obtain a mixture of diastereomers of an allene-1,3-dicarboxylic acid ester derivative, and then subjecting the mixture of diastereomers to cooling and crystallization in the presence of a basic substance to obtain (R)-allene-1,3-dicarboxylic acid ester derivative or (S)-allene-1,3-dicarboxylic acid ester derivative.

9. The method for synthesis of an optically active allene-1,3-dicarboxylic acid ester derivative according to claim 6, wherein the optically active alcohol is a member selected from the group consisting of (−)-menthol, (+)-menthol, (+)-isomenthol, (−)-8-phenylmenthol, (S)-(+)-6,6'-dibromo-1,1'-bi-2-naphthol, (S)-(+)-6,6'-dibromo-1,1'-bi-2-naphthol monomethyl ether, (R)-(−)-6,6'-dibromo-1,1'-bi-2-naphthol, (R)-(−)-6,6'-dibromo-1,1'-bi-2-naphthol monomethyl ether, (R)-(+)-1,1'-bi(2,2'-naphthol), (R)-(+)-1,1'-bi(2,2'-naphthol) monomethyl ether, (S)-(−)-1,1'-bi(2,2'-naphthol) and (S)-(−)-1,1'-bi(2,2'-naphthol)monomethyl ether.

10. The method for synthesis of an optically active allene-1,3-dicarboxylic acid ester derivative according to claim 8 or 9, wherein the dehydrating agent is 2-chloro-1,3-dimethylimidazolium chloride or 2-chloro-1,3-dimethylimidazolinium hexafluorophosphate.

11. The method for synthesis of an optically active allene-1,3-dicarboxylic acid ester derivative according to claim 8 or 9, wherein the basic substance is a tertiary amine.

12. A method for synthesis of an optically active 7-azabicyclo[2.2.1]heptan-2-one derivative which consists essentially of subjecting an optically active allene-1,3-dicarboxylic acid ester derivative and a dienophile to Diels-Alder reaction, in the presence of a Lewis acid, to obtain an optically active 7-azabicyclo[2.2.1]heptene derivative represented by the formula (3), or its enantiomer represented by the formula (4), then selectively reducing the isolated olefin of the derivative obtained above, and subjecting the resulting product to ozone decomposition to obtain a ketoester compound of an optically active 7-azabicyclo[2.2.1]heptane derivative represented by the formula (5), or its enantiomer represented by the formula (6),

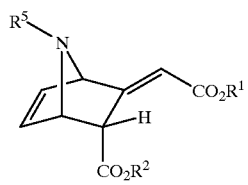

(3)

wherein $R^1$ and $R^2$ are each a group derived from an optically active alcohol and $R^5$ is a protective group for an amino group,

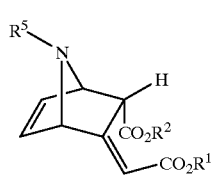

(4)

wherein $R^1$ and $R^2$ are each a group derived from an optically active alcohol and $R^5$ is a protective group for an amino group,

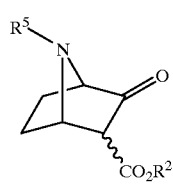

(5)

wherein $R^2$ is a group derived from an optically active alcohol and $R^5$ is a protective group for an amino group,

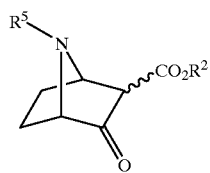

(6)

wherein $R^2$ is a group derived from an optically active alcohol and $R^5$ is a protective group for an amino group.

13. A method for synthesis of an optically active 7-azabicyclo-[2.2.1]heptan-2-one represented by the formula (7), or its enantiomer represented by formula (7)', which consists essentially of further subjecting the ketoester compound of an optically active 7-azabicyclo[2.2.1]heptane derivative represented by the formula (5) or its enantiomer represented by the formula (6) according to claim 10 to hydrolysis and decarbonation,

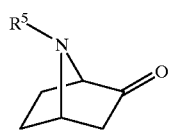

(7)

wherein $R^5$ is a protective group for an amino acid,

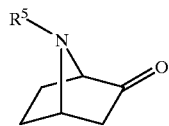

(7)′ wherein $R^5$ is a protective group for an amino acid.

* * * * *